United States Patent [19]

Weber et al.

[11] Patent Number: 5,143,679
[45] Date of Patent: Sep. 1, 1992

[54] METHOD FOR SEQUENTIALLY STRETCHING ZERO STRAIN STRETCH LAMINATE WEB TO IMPART ELASTICITY THERETO WITHOUT RUPTURING THE WEB

[75] Inventors: Gerald M. Weber, Loveland; James W. Richardson, Cincinnati, both of Ohio

[73] Assignee: The Procter & Gamble Company, Cincinnati, Ohio

[21] Appl. No.: 662,543

[22] Filed: Feb. 28, 1991

[51] Int. Cl.[5] ............................................. B29C 55/04
[52] U.S. Cl. ............................... 264/288.8; 264/290.2
[58] Field of Search ................ 264/288.4, 288.8, 290.2

[56] References Cited

U.S. PATENT DOCUMENTS

| | | | |
|---|---|---|---|
| Re. 19,494 | 3/1935 | Glidden et al. ........................ 154/2 |
| 375,073 | 4/1887 | Kayser ................................ 428/138 |
| 1,620,162 | 3/1927 | Martin ................................ 428/138 |
| 2,068,456 | 1/1937 | Hooper ................................ 154/2 |
| 2,075,189 | 3/1937 | Galligan et al. ..................... 154/33 |
| 2,077,438 | 4/1937 | Rowe ................................... 154/33 |
| 2,697,678 | 12/1954 | Ness et al. ......................... 154/101 |
| 3,025,199 | 3/1962 | Harwood ............................. 154/46 |
| 3,214,323 | 10/1965 | Russell et al. ..................... 161/148 |
| 3,255,065 | 6/1966 | Wyckoff ............................. 156/229 |
| 3,261,903 | 7/1966 | Carr .................................... 264/289 |
| 3,305,911 | 2/1967 | Chapman et al. ..................... 28/72 |
| 3,316,136 | 4/1967 | Pufahl ................................ 156/160 |
| 3,438,106 | 4/1969 | Cohn et al. .......................... 28/74 |
| 3,545,054 | 12/1970 | Sando et al. ......................... 26/51 |
| 3,574,809 | 4/1971 | Fairbanks et al. .................. 264/167 |
| 3,575,782 | 4/1971 | Hansen .............................. 161/141 |
| 3,650,882 | 3/1972 | Thomas .............................. 161/122 |
| 3,655,502 | 4/1972 | Yoshikawa ......................... 161/127 |
| 3,687,754 | 8/1972 | Stumpf ................................ 156/72 |
| 3,687,797 | 8/1972 | Wideman ........................... 161/129 |
| 3,694,815 | 10/1972 | Burger ................................. 2/224 |
| 3,708,361 | 1/1973 | Stumpf ................................ 156/72 |
| 3,728,203 | 4/1973 | Taylor ................................. 161/39 |
| 3,791,911 | 2/1974 | Yaeger et al. ....................... 161/58 |
| 3,816,228 | 6/1974 | Stumpf ................................ 161/63 |
| 3,819,401 | 6/1974 | Massengale et al. ................ 156/85 |
| 3,842,832 | 10/1974 | Wideman et al. ................... 128/169 |
| 3,849,526 | 11/1974 | Muller et al. ....................... 264/286 |
| 3,860,003 | 1/1975 | Buell .................................. 128/287 |
| 3,949,127 | 4/1976 | Ostermeier et al. ................ 428/137 |
| 3,949,128 | 4/1976 | Ostermeier ......................... 428/152 |
| 3,953,566 | 4/1976 | Gore .................................. 264/288 |
| 3,968,287 | 7/1976 | Balk ................................... 428/136 |
| 3,991,250 | 11/1976 | Hartmann et al. ................... 428/288 |
| 4,048,364 | 9/1977 | Harding et al. ..................... 428/113 |
| 4,081,301 | 3/1978 | Buell .................................. 156/164 |

(List continued on next page.)

Primary Examiner—James Lowe
Attorney, Agent, or Firm—E. Kelly Linman; Thomas H. O'Flaherty; Richard C. Witte

[57] ABSTRACT

An improved method and apparatus for incrementally stretching "zero strain" stretch laminate webs to impart elasticity thereto in the direction of stretching, at least up to the point of initial stretching. The "zero strain" stretch laminate material is formed of at least two plies of material which are either intermittently or substantially continuously secured to one another along at least a portion of their coextensive surfaces while in a substantially untensioned ("zero strain") condition. One of the plies is stretchable and elastomeric, while the second ply is elongatable, but not necessarily elastomeric. The second ply will, upon stretching of the laminate, be at least to a degree permanently elongated so that, upon release of the applied tensile forces, it will not return to its original undistorted configuration. This results in z-direction bulking of the laminate web when the applied tension is released as well as subsequent elastic extensibility in the direction of initial stretching, at least up to the point of initial stretching. In a particularly preferred embodiment of the present invention, the mechanical stretching operation is carried out by passing said laminate web between multiple pairs of meshing corrugated rolls, each pair of rolls exhibiting a greater degree of meshing than the preceding pair, to sequentially stretch said web in stages. Sequentially stretching the web in the foregoing manner minimizes damage to the web.

22 Claims, 7 Drawing Sheets

U.S. PATENT DOCUMENTS

| | | | |
|---|---|---|---|
| 4,087,226 | 5/1978 | Mercer | 425/397 |
| 4,107,364 | 8/1978 | Sisson | 428/196 |
| 4,116,892 | 9/1978 | Schwarz | 264/288.8 |
| 4,194,041 | 3/1980 | Gore et al. | 428/315 |
| 4,209,563 | 6/1980 | Sisson | 428/288 |
| 4,223,059 | 9/1980 | Schwarz | 428/198 |
| 4,223,063 | 9/1980 | Sabee | 428/224 |
| 4,239,578 | 12/1980 | Gore | 156/361 |
| 4,251,585 | 2/1981 | Schwarz | 264/288.8 |
| 4,277,429 | 7/1981 | Okita | 264/127 |
| 4,297,157 | 10/1981 | Van Vliet | 156/164 |
| 4,333,782 | 6/1982 | Pieniak | 156/164 |
| 4,337,771 | 7/1982 | Pieniak et al. | 128/287 |
| 4,342,314 | 8/1982 | Radel et al. | 128/287 |
| 4,351,872 | 9/1982 | Brosseau et al. | 428/198 |
| 4,368,233 | 1/1983 | Barkis et al. | 428/245 |
| 4,368,565 | 1/1983 | Schwarz | 26/99 |
| 4,414,970 | 11/1983 | Berry | 128/156 |
| 4,418,123 | 11/1983 | Bunnelle et al. | 428/517 |
| 4,443,511 | 4/1984 | Worden et al. | 428/198 |
| 4,446,189 | 5/1984 | Romanek | 428/152 |
| 4,464,815 | 8/1984 | Canterino | 26/72 |
| 4,475,971 | 10/1984 | Canterino | 156/163 |
| 4,517,714 | 5/1985 | Sneed et al. | 28/103 |
| 4,525,407 | 6/1985 | Ness | 428/138 |
| 4,543,099 | 9/1985 | Bunnelle et al. | 604/385 A |
| 4,556,596 | 12/1985 | Meuli | 428/152 |
| 4,578,133 | 3/1986 | Oshefsky et al. | 156/164 |
| 4,606,964 | 8/1986 | Wideman | 428/152 |
| 4,629,525 | 12/1986 | Rasmussen | 156/84 |
| 4,652,322 | 3/1987 | Lim | 264/288.8 |
| 4,652,487 | 3/1987 | Morman | 428/138 |
| 4,657,802 | 4/1987 | Morman | 428/152 |
| 4,660,261 | 4/1987 | Corbiere | 28/155 |
| 4,675,016 | 6/1987 | Meuli et al. | 604/385 |
| 4,692,368 | 9/1987 | Taylor et al. | 428/137 |
| 4,720,415 | 1/1988 | VanderWielen et al. | 428/152 |
| 4,725,473 | 2/1988 | VanGompel et al. | 428/156 |
| 4,741,944 | 5/1988 | Jackson et al. | 428/152 |
| 4,813,946 | 3/1989 | Sabee | 604/385.2 |
| 4,834,741 | 5/1989 | Sabee | 604/385.2 |
| 4,857,067 | 8/1989 | Wood et al. | 604/389 |
| 4,981,747 | 1/1991 | Morman | 428/198 |

FOREIGN PATENT DOCUMENTS

| | | | |
|---|---|---|---|
| 2503775 | 8/1976 | Fed. Rep. of Germany | 264/290.2 |
| 3621205 | 1/1988 | Fed. Rep. of Germany | . |

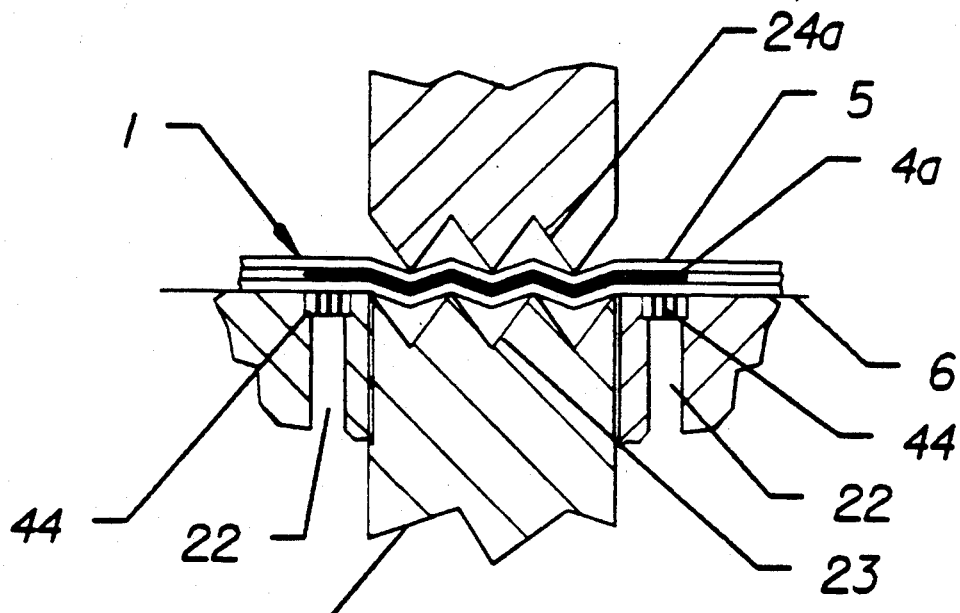
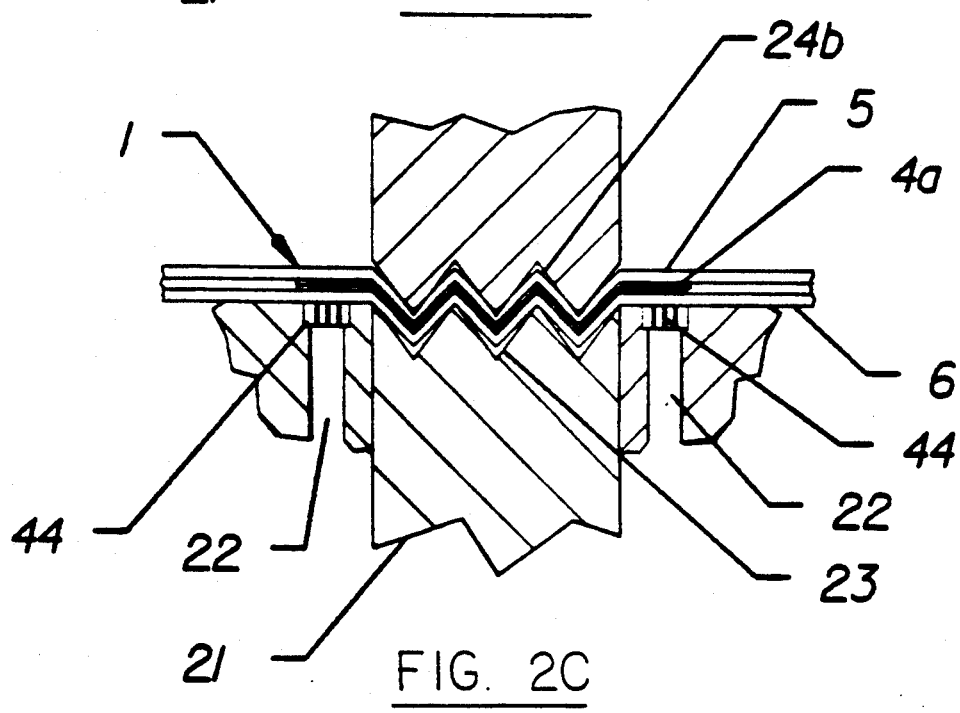

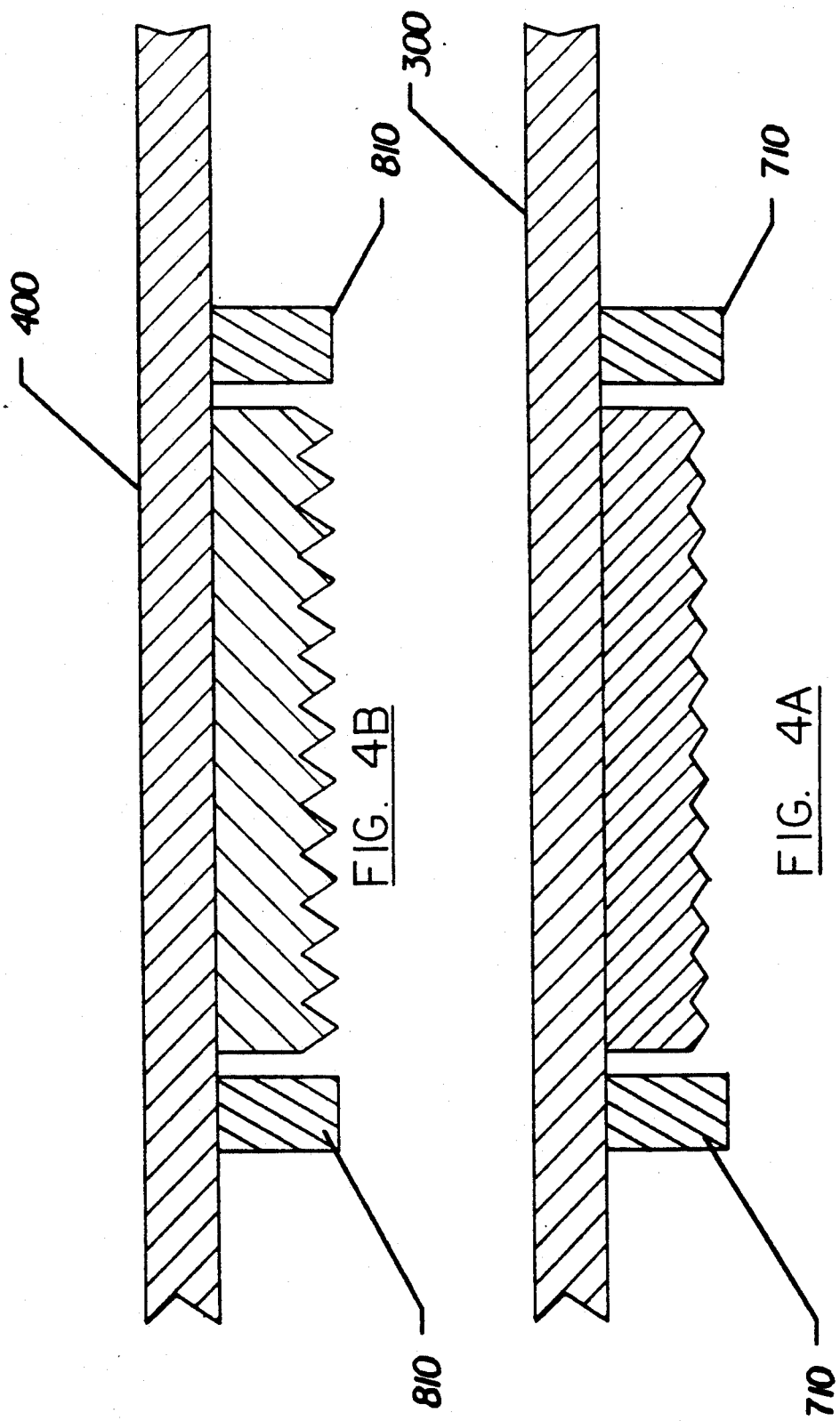

METHOD FOR SEQUENTIALLY STRETCHING ZERO STRAIN STRETCH LAMINATE WEB TO IMPART ELASTICITY THERETO WITHOUT RUPTURING THE WEB

TECHNICAL FIELD

The present invention has relation to a "zero-strain"-stretch laminate web which is assembled in a substantially untensioned (i.e., "zero-strain") condition and which is capable of being rendered elastic by mechanical stretching.

The present invention has further relation to method and apparatus for producing such a "zero-strain" stretch laminate web, wherein predetermined portions of said web can be rendered elastic by mechanical stretching.

The present invention, in a particularly preferred embodiment, has further relation to method and apparatus for rendering predetermined portions of such a "zero-strain" stretch laminate web elastic in one or more directions while the web is moving continuously at high speed in the machine direction.

The present invention has further relation to such a "zero strain" stretch laminate web comprising a multiplicity of absorbent articles, such as single use diapers, connected one to another along their waistband portions, each of the diapers in said web further including at least one elastomeric element secured to either the topsheet, the backsheet or both while said elastomeric element is in a substantially untensioned condition, at least a portion of the web containing said substantially untensioned elastomeric element being subjected to mechanical stretching which is sufficient to permanently elongate the web to which said elastomeric element is secured. To the extent that it is not secured to the elastomeric element, said permanently elongated web undergoes z-direction bulking between adjacent points of securement to the elastomeric element in a direction perpendicular to the plane of the elastomeric element when the tensile forces are released and said elastomeric element returns to its substantially untensioned configuration. Regardless of the degree of z-direction bulking, the "zero-strain" stretch laminate portion of the web is thereafter elastically extensible in the direction of initial stretching, at least up to the point of initial stretching.

The present invention, in a particularly preferred embodiment, has further relation to such method and apparatus wherein the mechanical stretching of said laminate web is carried out by passing said laminate web between multiple pairs of meshing corrugated rolls to sequentially stretch said web without causing substantial damage thereto.

The present invention has further relation, in a particularly preferred embodiment, to a single use absorbent bandage structure, such as a diaper, having discrete elasticized portions thereof formed by the method and apparatus of the present invention.

BACKGROUND ART

In simplest terms, a "zero-strain" stretch laminate web, as those terms are used herein, refers to a laminate web comprised of at least two plies of material which are secured to one another, either intermittently or substantially continuously, along at least a portion of their coextensive surfaces while in a substantially untensioned ("zero-strain") condition. At least one of said plies is preferably in the form of a continuous web to facilitate continuous, high speed processing. The other of said plies may comprise a continuous web or discrete elements or patches secured to the continuous web at predetermined locations.

As used in the foregoing context, an "intermittently" bonded laminate web shall mean a laminate web wherein prior to the application of tension the plies are initially bonded to one another at discrete spaced apart points or one wherein the plies are substantially unbonded to one another in discrete spaced apart areas. Intermittently bonded laminate webs of the first type can be formed by passing two heat bondable plies through a heated patterned embossing roll nip or by applying discrete spaced apart areas of adhesive to one of the plies before bringing it in contact with the other ply, while an intermittently bonded web of the second type can be formed by feeding an adhesively coated apertured ply or scrim between a pair of substantially continuous plies. Conversely, a "substantially continuously" bonded laminate web shall mean a laminate web wherein prior to the application of tension the plies are initially bonded substantially continuously to one another throughout their areas of interface. Substantially continuously bonded laminate webs can be formed by extruding a first substantially continuous, thermoplastic adhesive ply directly onto a second ply while the first ply is in a heated condition, passing two heat bondable plies between a heated smooth surfaced roll nip or by applying a substantially continuous adhesive coating, spray or densely patterned melt blown to one of the plies prior to bringing it in contact with the other ply.

One of the plies employed in a "zero-strain" stretch laminate web of the present invention is comprised of a material which is stretchable and elastomeric, i.e., it will return substantially to its untensioned dimensions after an applied tensile force has been released. The second ply secured to the elastomeric ply is elongatable, most preferably drawable, but is not necessarily elastomeric. Whatever its composition, the second ply will, upon stretching, be at least to a degree permanently elongated so that upon release of the applied tensile forces, it will not fully return to its original undistorted configuration. To the extent that the permanently elongated second ply is not secured to the elastomeric web after the stretching operation, the permanently elongated second ply expands in the z-direction between its points of securement to the elastomeric web when the elastomeric web to which it is secured returns to its substantially undistorted configuration in the x-y plane. The greater the distance between the adjacent points of securement in the x-y plane after stretching, the greater will be the degree of z-direction expansion in the resultant laminate web. Regardless of the degree of z-direction expansion, the resulting "zero-strain" stretch laminate web is thereafter elastically extensible in the direction of initial stretching, at least up to the point of initial stretching.

While the term "zero-strain", which is used herein to describe stretch laminate webs to which the present invention pertains, has not to Applicant's knowledge been used by prior art workers to describe webs of the aforementioned type, it will for consistency be hereinafter used throughout the present specification to describe such webs.

One very early execution of an intermittently bonded "zero strain" stretch laminate web is disclosed in U.S. Pat. No. 2,075,189 issued to Galligan et al. on Mar. 30, 1937. According to the disclosure of the aforementioned Galligan et al. patent, two superposed continuous plies of rubber, one of which is under tension and longitudinally stretched, are passed between a pair of pressure rolls traveling at the same peripheral speed. One of the rolls is provided with relatively small or narrow projections in a desired pattern, which projections cooperate with the second roll to press together into adhesive contact small portions of the two plies of rubber so that relatively closely spaced small areas of the superposed plies will be united in a pattern similar to that of the projections on the pressure roll.

According to Galligan et al., the roll cooperating with the roll having projections may be smooth, or instead it may be provided with mating projections similar to those on the other roll. The rolls are spaced apart, depending upon the combined thickness of the two plies of rubber, to a degree sufficient to provide the desired uniting pressure without undesirably thinning the rubber of the joined areas.

Upon issuance of the joined plies from the rolls, the tension on the stretched ply is relaxed, and as a result this ply contracts in length and also slightly expands in width. Since the unstretched ply intermittently bonded thereto cannot thus contract, it is drawn up from a longitudinal direction in puckers or crinkles 4. In the specific embodiment shown in FIGS. 1 and 2 of Galligan et al., the top or crinkled ply is designated by the numeral 1, while the stretched or backing ply is designated by the numeral 2. At 3 there appear narrow parallel joint lines at the points where the two plies have been united by the pressure.

In a succeeding step of the process disclosed in the Galligan et al. patent, the foregoing intermittently bonded composite comprising a two ply crinkled material is very highly stretched in a lateral direction (substantially parallel to the joint lines 3), the tension being sufficient to stretch the top crinkled ply 1 beyond its elastic limit. However, the applied tension remains within the elastic limit of the bottom or backing ply 2. If desired, the lateral stretching may be to a point as high as eight times the original width of the undistorted composite.

Since the top ply 1 is laterally stretched beyond its elastic limit, its crinkles 4 are necessarily permanently thinned out in a lateral direction so that when the lateral tension on the laminate sheet is released, the superficial area of the material in any crinkle, when spread flat, will be much greater than that of the corresponding portion of the backing ply 2. As a result, when the backing ply 2 laterally contracts, the crinkles 4 on the top ply 1 are drawn up from a lateral direction, and since their superficial area is much greater than before, the contracting effect of the backing ply causes the crinkles to assume a highly irregular and distorted form between the joint lines 3, i.e., it produces z-direction bulking of the composite, as generally shown in FIGS. 5, 6 and 7. Galligan et al. suggest that the resultant "zero-strain"stretch laminate material is particularly suitable for use in the making of bathing suits, bathing caps, shoes, aprons and other articles.

Another early execution of an intermittently bonded "zero strain" stretch laminate web, which is specifically suggested for uses such as toweling, wiping material and expendable garment material, is disclosed in U.S. Pat. No. 3,025,199 issued to Harwood on Mar. 13, 1962. In particular, Harwood suggests the formation of a scrim comprised of intersecting sets of threads or filaments 2 and 3 which are bonded to one another at their points of intersection to form a reticulated reinforcing network 1. A pair of nonwoven layers 4 and 5 of fibers are preferably attached to the opposite sides of the reinforcing network 1 formed by the intersecting threads.

The laminate web structure disclosed by Harwood is thereafter subjected to a stretching operation in one or more directions to permanently expand the nonwoven webs 4,5 secured to the opposed surfaces of the reinforcing network 1. According to Harwood, this may be carried out by stretching the laminate web crosswise (i.e., in the cross-machine direction) via suitable roll means or by appropriately guided conveyor chains equipped with means for gripping and applying opposed tensile forces to the side margins of the web (i.e., tentering apparatus). If lengthwise stretching of the laminate web is desired, Harwood teaches that this may be effected by cooperative low and high speed roll pairs.

Since the threads 2,3 used to form the reticulated reinforcing network 1 of Harwood are, in a particularly preferred embodiment, resilient, the network 1 tends to restore itself to a predetermined substantially undistorted configuration as soon as any tensile forces which have been applied to the laminate web are removed. As a result, the permanently expanded outermost plies 4 and 5 shown in the cross-section of FIG. 4 of the Harwood patent exhibit z-direction bulking in the unbonded areas 6 which coincide with the openings in the resilient network 1.

More recent executions of both intermittently bonded and substantially continuously bonded "zero-strain"-stretch laminate webs comprised of synthetic polymer plies and intended for single use or disposable apparel applications are disclosed in commonly assigned U.S. Pat. No. 4,107,364 issued to Sisson on Aug. 15, 1978 and commonly assigned U.S. Pat. No. 4,209,563 issued to Sisson on Jun. 24, 1980. The commonly assigned Sisson patents, which are hereby incorporated herein by reference, teach that the "zero-strain"stretch laminate webs therein disclosed are particularly well suited for single use apparel applications because of their relatively low cost compared to conventional cloth materials. The Sisson patents further teach that such "zero-strain"-stretch laminates may be constructed in many different forms ranging from extremely lightweight versions suitable for lingerie applications to heavier versions suitable for apparel waistband applications.

In a preferred embodiment, Sisson's "zero-strain"-stretch laminate comprises at least one ply comprised substantially of synthetic polymeric filaments which are relatively elastomeric and at least one ply comprised substantially of synthetic polymeric filaments which are relatively elongatable but relatively nonelastic. In a particularly preferred embodiment the plies are bonded to one another to form a coherent laminate web.

As pointed out earlier herein, Sisson discloses two types of web bonding configurations: substantially continuous bonding, as can be accomplished via a heated smooth roll nip; and substantially intermittent bonding at a plurality of spaced apart points, as can be accomplished via a heated patterned embossing roll nip.

Laminate webs employing either bonding configuration are thereafter mechanically worked as by stretching, preferably substantially uniformly, in at least one direction followed by substantially complete relaxation to develop a low modulus of elasticity in the direction of stretching. In the case of the intermittently bonded laminate webs, the elongatable but relatively nonelastic ply is permanently elongated by the stretching operation. Accordingly, it is bulked and bunched between the intermittent bonds securing it to the relatively elastomeric ply when the applied tension is released, i.e., it is bulked to a significant degree in the z-direction to produce a "zero-strain" stretch laminate web which is elastically extensible in the direction of initial stretching, at least up to the point of initial stretching. In the case of the substantially continuously bonded laminate webs, the permanently elongated polymeric filaments which are relatively inelastic do not retract when tension is released on the laminate web. Consequently they are caused to undergo looping, bulking and bunching on a much finer scale, i.e., between their bond points to the relatively elastomeric polymeric filaments when tension is released on the laminate web. While the z-direction bulking is less pronounced in such continuously bonded laminate webs, "zero-strain" stretch laminate webs of the latter type are also elastically extensible in the direction of stretching, at least up to the point of initial stretching.

Numerous examples of "zero-strain" stretch laminate webs employing either continuous or intermittent bonding configurations and methods for producing such webs are disclosed in the aforementioned commonly assigned Sisson patents.

Sisson's suggestion to employ "zero-strain" stretch laminate materials in single use or disposable items of wearing apparel has been followed by a number of subsequent workers in the art. See, for example, U.S. Pat. No. 4,525,407 issued to Ness on Jun. 25, 1985, which discloses disposable diapers and surgical gowns incorporating one or more "zero-strain" stretch laminate composites comprised of an untensioned elastic member intermittently bonded to an unstretched less extensible substrate, the resulting laminate being rendered elastic by stretching.

FIGS. 1-3 of Ness disclose a simple two layer "zero strain" stretch laminate web which is intended for use as an elastic bandage or wrap. The laminate web comprises a nonapertured elastic member 10 and an unstretched, nongathered substrate 12, which before it is stretched, is less easily extensible than the elastic member and which has less elastic recovery than the elastic member. The substrate and the elastic member are intermittently bonded at spaced apart points 14 in a regular or irregular pattern. The laminate web is thereafter stretched in the directions of the arrows shown in FIG. 2. Upon release of the applied tensile forces, the elastic member 10 causes puckering, i.e., z-direction bulking, of the permanently elongated substrate 12 between bonding points 14, as generally shown in FIG. 3. Like the aforementioned "zero-strain" stretch laminate webs of Galligan et al., Harwood and Sisson, the resultant laminate web disclosed by Ness is thereafter elastically extensible in the direction of initial stretching, at least up to the point of initial stretching.

Another elastic composite web embodiment 30 is illustrated in FIGS. 5-8 of Ness. The latter embodiment employs a reticulated elastic element 20 having transverse strands 22 and longitudinal strands 24. The reticulated elastic element 20 of Ness appears to be generally similar to the resilient reticulated reinforcing member 1 disclosed in FIGS. 1-4 of the aforementioned Harwood patent. Like Harwood, Ness also employs a first substrate 28 having less extensibility than the elastic member 20 and less elastic recovery than the elastic member.

A second substrate 30, which has substantially the same physical properties as substrate 28, and which "sandwiches" the elastic member 10, is also employed by Ness.

Substrates 28 and 30 of Ness are secured at least to the opposing surfaces of the reticulated elastic member 20 while the elastic member is in a substantially untensioned condition. The substrates 28 and 30 may, if desired, also be bonded to one another through the openings in the reticulated elastic member. According to the teachings of Ness, when the laminate web is thereafter stretched in the longitudinal direction, the substrates 28,30 undergo permanent elongation and may become delaminated from one another, but remain intermittently bonded to the reticulated elastic member 20 at the intermediate sites comprising the transverse and/or longitudinal strands of the reticulated member. Once tension on the web has been released, the reticulated elastic member 20 restores the web to the substantially undistorted configuration of the reticulated elastic member 20, thereby causing z-direction bulking of the permanently elongated substrates 28,30 between their spaced apart points of securement to the longitudinal strands 22 of the elastic member in a direction substantially perpendicular to the direction of stretching. The cross-section of the resultant elastic composite web of Ness shown in FIG. 9 is generally similar to that of the "zero-strain" stretch laminate web shown in FIG. 4 of the aforementioned Harwood patent.

In addition to the foregoing "zero-strain" stretch laminate web embodiments, FIGS. 9-12 of the Ness patent disclose the use of the elastic composite materials to provide extensible legband portions 136,137 and extensible waistband portions 138,139 along the opposed side edges and ends, respectively, of a disposable diaper. Such elastic composite materials may be incorporated into garments or bandages during manufacture and may, if desired, be stretched to provide subsequent elastic extensibility in the direction of initial stretching. According to Ness, the latter stretching operation may either be performed by the end user or applier of the product as it is being applied or it may be stretched during the manufacturing process.

An automated method for stretching a laminate web comprising a reticulated elastic 210 heat sealed to a pair of opposing plastic film layers 214,216 is disclosed in FIG. 14 of Ness. In the disclosed embodiment, the three layers comprising the composite are fed into a nip formed between a pair of smooth, heated, counter-rotating rolls 224,226 to heat seal the reticulated elastic to the two layers of film 214,216 to form a heat sealed three-layer composite 228. The heat sealed composite 228 is then fed into the nip formed between a second pair of counter-rotating rolls 230,232 which may be cooled to ensure that the thermal bonding is "set". The composite web 234 emerging from the second pair of counter-rotating rolls 230,232 is then fed into the nip of a third pair of counter-rotating rolls 236,238 rotating at a faster peripheral speed than the second pair of counter-rotating rolls 230,232 to effect drafting of the composite web 234 between the two pairs of rolls.

According to Ness, this drafting stretches the films 214,216 and ruptures the heat seal bonds which were previously formed between the films 214,216 through the apertures in the reticulated elastic scrim. Stretching the composite with elastic in the longitudinal direction may also, according to Ness, rupture the seal between the longitudinal strands and the film(s), leaving only the transverse strands bonded to the film layers 214,216. As the stretched composite 244 emerges from the third pair of counter-rotating rolls 236,238, the longitudinal or machine direction tension is relaxed and the composite 244 is fed to a windup 246 that is rotating at a peripheral speed approximately equal to the peripheral speed of the second pair of counter-rotating rolls 230 and 232.

While stretching a laminate web by applying tension to widely separated points of support, e.g., first roll pair 230,232 and second roll pair 236,238, does serve to permanently elongate the substantially inelastic film plies 214,216, Applicant has learned that the uniformity of elongation in such a "zero-strain"stretch laminate web, as measured along the unsupported portion of the composite web 234, decreases as the distance between the first roll pair 230,232 and the second roll pair 236,238 increases. For any given distance between the first and second roll pairs, this nonuniformity becomes more pronounced as the difference in peripheral speed between the second roll pair 236,238 and the first roll pair 30,232 increases, i.e., as the composite web 234 undergoes a greater degree of stretching.

Applicant has further learned that these nonuniformity problems can be avoided or at least minimized by following one of the specific suggestions set forth in the aforementioned commonly assigned Sisson patents. Namely, to incrementally stretch the "zero strain" stretch laminate material by passing it through an incremental stretching system, such as the nip formed between a pair of meshing corrugated rolls which have an axis of rotation substantially perpendicular to the direction of web travel. The meshing corrugated rolls support the laminate web at plural closely spaced apart locations corresponding to the width of the corrugations during the stretching operation. This causes substantially uniform incremental stretching of each unsupported segment of the web between adjacent support points rather than highly localized stretching as often occurs when only the outermost extremities of the web are subjected to tension.

Sisson's suggestion to incrementally stretch a "zero strain" stretch laminate material by passing it between corrugated rolls to impart elastic extensibility thereto has also been followed by at least one subsequent worker in the art. See, for example, U.S. Pat. No. 4,834,741 issued to Sabee on May 30, 1989 and hereby incorporated herein by reference.

Sabee, like Ness, discloses a single use garment, such as a disposable diaper, employing a "zero-strain"stretch laminate material comprising an untensioned elastomeric element secured between a pair of drawable elements in its opposed waistband and legband portions. The elastic elements 41 shown in FIG. 1 of Sabee are affixed in the waistband portions of the diaper web while in a substantially relaxed condition to a drawable topsheet web, a drawable backsheet web or both. The bonding configuration employed by Sabee may be either intermittent, as by passing the laminate material through a pressure nip formed between two rolls, one of which is heated and contains a plurality of raised points on its surface, or continuous, as by depositing a thin band of viscoelastic hot melt pressure sensitive adhesive onto one of the webs and thereafter pressing the hot melt pressure sensitive adhesive to the other web by passing the laminate through a pressure nip formed between a pair of smooth surfaced rolls.

Regardless of which bonding configuration is employed, the portions of the diaper web containing elastic web elements 41 are thereafter laterally stretched in the cross-machine direction by the meshing corrugations on pairs of corrugated rolls 31, as generally shown in Sabee's FIGS. 5 and 6. Simultaneously the coinciding portions of the drawable topsheet and backsheet webs in the area of elastic element attachment are incrementally stretched and drawn to impart a permanent elongation and molecular orientation thereto in the cross-machine direction. Because corrugated rolls 31 have their meshing corrugations aligned substantially parallel to the machine direction, incremental stretching of the web takes place in the cross-machine direction. Accordingly, the fully processed waistband portions of Sabee's diaper web are thereafter elastically extensible in the cross-machine direction, at least up to the point of initial stretching.

A similar machine direction stretching operation is preferably carried out with respect to the opposed legbands, which include untensioned elastic elements 42, by passing the diaper web of Sabee between another pair of meshing corrugated rolls 89, as generally shown in FIGS. 12 and 13. Because corrugated rolls 89 have their meshing corrugations aligned substantially parallel to the cross-machine direction, incremental stretching of the web takes place in the machine direction. Accordingly, the legband portions of Sabee's diaper web are thereafter elastically extensible in the machine direction, at least to the point of initial stretching.

While Sisson's suggestion to use corrugated rolls to incrementally stretch a "zero-strain"stretch laminate web has been found to work reasonably well when the desired degree of stretching, and hence extensibility, is relatively small, the present Applicant has discovered that for higher degrees of incremental stretching there is a tendency for the corrugated rolls to cause damage to the web. In extreme situations, this damage can even take the form of rupturing one or more of the webs comprising the "zero-strain"stretch laminate in the pattern of the corrugations. Depending upon the desired characteristics in the final product, e.g., fluid-imperviousness, such damage can render the resultant "zero strain" stretch laminate web unsuitable for its intended purpose.

The aforementioned problems become more and more serious as the speed of web processing and the desired degree of incremental stretching increase and the elongation to rupture characteristic of the stretch laminate web in question decreases.

OBJECTS OF THE INVENTION

Accordingly, it is an object of the present invention to provide improved method and apparatus for incrementally stretching "zero-strain"stretch laminate webs to a greater degree while minimizing damage to the webs.

It is another object of the present invention, in a preferred embodiment, to provide improved method and apparatus for sequentially stretching such webs using multiple pairs of meshing corrugated rolls to reduce the strain rate experienced by the webs as they pass between each pair of meshing corrugated rolls.

It is another object of the present invention, in a particularly preferred embodiment, to provide such improved method and apparatus capable of producing "zero-strain"stretch laminate webs exhibiting an increased degree of incremental stretching, and hence elastic extensibility, with less damage than has previously been obtainable with a single set of meshing corrugated rolls operating at comparable web speeds.

DISCLOSURE OF THE INVENTION

The present invention comprises improved method and apparatus for incrementally stretching a "zero-strain" stretch laminate web to impart elasticity thereto in the direction of initial stretching, at least up to the point of initial stretching. While "zero-strain" stretch laminate webs per se are generally known in the art as is the use of meshing corrugated rolls to incrementally stretch such "zero-strain" stretch laminate webs to impart elasticity thereto, the present Applicant has discovered that for some "zero strain" stretch laminate webs there is a tendency for the corrugated rolls to cause damage to the webs, particularly when relatively high degrees of incremental stretching are involved. In extreme situations, this damage can even take the form of rupturing of the webs in the pattern of the corrugations.

The present Applicant has found a way to eliminate or at least reduce the severity of the foregoing problem in many of the "zero-strain" stretch laminate webs which exhibit this behavior. In a preferred embodiment this is accomplished by providing method and apparatus for sequentially stretching the "zero-strain" stretch laminate portions of the web during the incremental stretching process. In a particularly preferred embodiment, the mechanical stretching operation is carried out in stages by passing said laminate web between multiple pairs of meshing corrugated rolls, each pair of rolls exhibiting a greater degree of meshing than the preceding pair, to sequentially stretch said web while minimizing damage thereto. The use of multiple roll pairs with progressively greater degrees of meshing imposes a lower strain rate on the web than would be the case for a single pair of meshing corrugated rolls having an amplitude and degree of meshing comparable to the final pair of multiple rolls. In addition, the temporary release of tension from the web as it passes between the successive roll pairs allows some degree of stress redistribution to occur in the web prior to the web's being incrementally stretched to a greater degree by each succeeding roll pair. Minimizing the strain rate and allowing a degree of stress redistribution in the foregoing manner minimizes the tendency to cause damage to the web.

BRIEF DESCRIPTION OF THE DRAWINGS

While the specification concludes with claims that particularly point out and distinctly claim the subject matter regarded as forming the present invention, it is believed that the invention will be better understood from the following detailed description with reference to the drawings in which:

FIG. 2B is a highly enlarged view taken at the inset 2B shown in FIG. 2, said view showing the degree of meshing of the first set of corrugated rolls with one another as the "zero-strain" stretch laminate portion of the diaper web passes therebetween;

FIG. 2C is a highly enlarged view taken at the inset 2C shown in FIG. 2, said view showing the degree of meshing of the second set of corrugated rolls with one another as the partially stretched "zero-strain" stretch laminate portion of the diaper web passes therebetween:

FIG. 4A is a simplified cross-sectional view taken along section line 4A—4A in FIG. 3; and FIG. 4B is a simplified cross-sectional view taken along section line 4B—4B in FIG. 3.

DETAILED DESCRIPTION OF THE PRESENT INVENTION

It will be readily apparent to those skilled in the art that although the following description of the present invention is in connection with a single use diaper structure having preselected elasticized areas, the present invention may be practiced with equal facility on nearly any web either comprised entirely of or containing discrete, isolated "zero-strain" stretch laminate portions.

Figure 1:
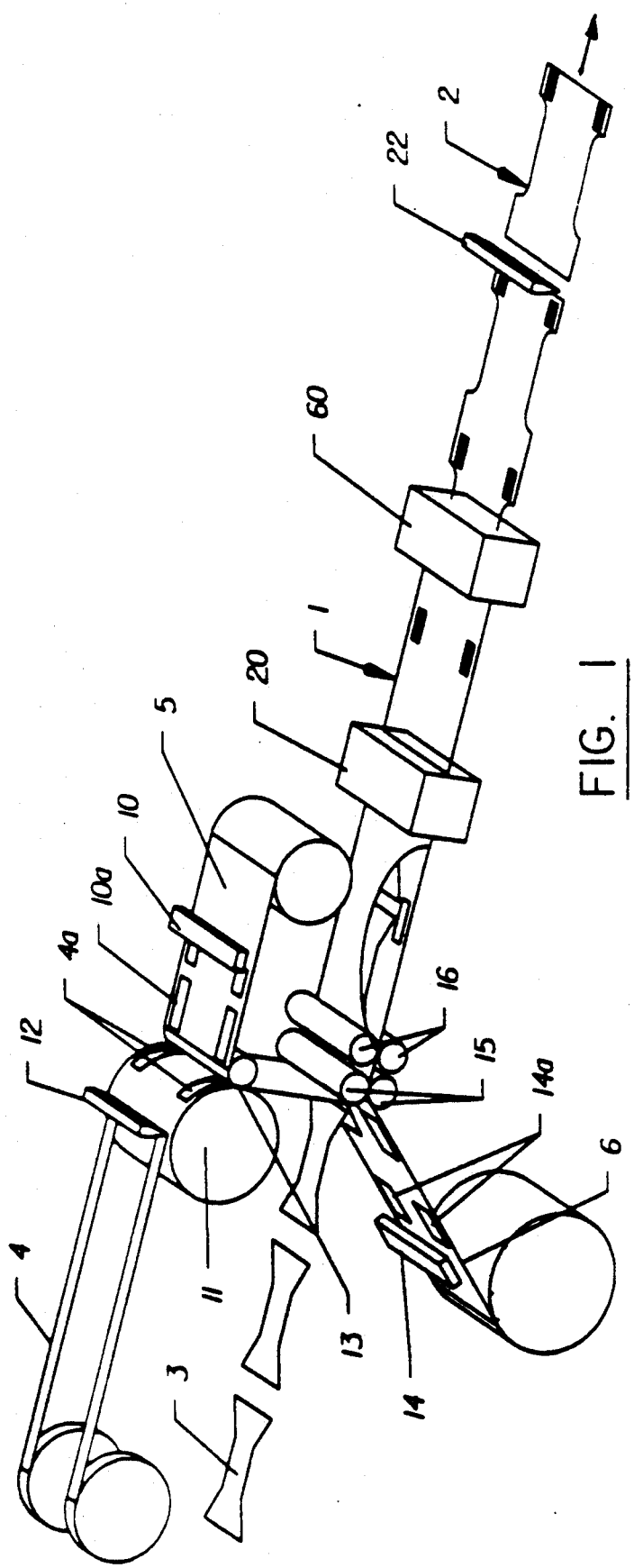
FIG. 1 is a simplified perspective view showing the assembly of a web of single use diapers, each having elastomeric patches secured thereto at regularly spaced locations along its length, said web being subjected to a sequential stretching process using multiple pairs of meshing corrugated rolls in the areas of said web coinciding with the elastomeric patches, said web also being cut at predetermined points along its length to form a multiplicity of single use diapers, each having at least one pair of laterally stretchable side panels.
Figure 2:
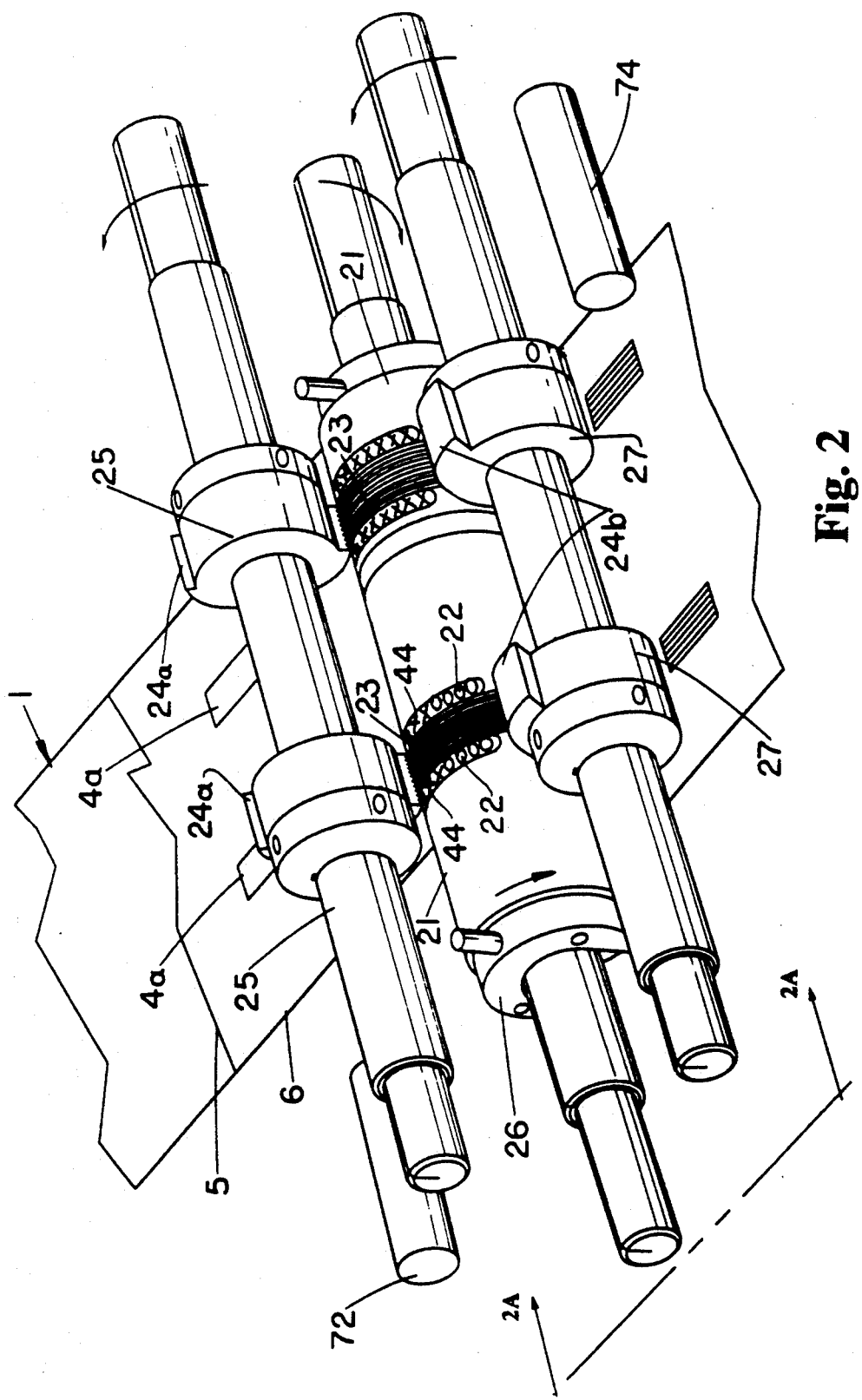
FIG. 2 is a simplified perspective view of a sequential web stretching assembly of the present invention, said assembly being comprised of two sequentially positioned sets of meshing corrugated rolls.

The diaper manufacturing process and the diapers, which are only schematically illustrated in Drawing FIGS. 1-2C, may, if desired, be generally similar to those disclosed in commonly assigned U.S. Pat. No. 4,081,301 issued to Buell on Mar. 28, 1978 and hereby incorporated herein by reference. However, the elasticized legbands of the Buell diaper are an option, and for clarity are not shown herein. The diaper web and the hourglass-shaped diapers schematically shown in FIGS. 1-2C employ elasticized side panels in one or both sets of the ear portions of the hourglass. Positioning of such discrete elastomeric elements which can be used to produce such elasticized side panels in at least one pair of ears is generally disclosed in U.S. Pat. No. 4,857,067 issued to Wood et al. on Aug. 15, 1989, which patent is also hereby incorporated herein by reference.

Referring to FIG. 1, there is shown a continuous web 1 comprised of a plurality of interconnected single use diapers 2. Each diaper is comprised of an absorbent pad element 3, a pair of elastomeric elements or patches 4a, which may be comprised of "live" synthetic or natural rubber, synthetic or natural rubber foam, elastomeric film, elastomeric nonwoven laminate, elastomeric scrim or the like, secured to the webs at predetermined spaced locations, said absorbent pad and said elastomeric patches being located intermediate a moisture-impervious backsheet 5, which is typically comprised of an elongatable polymeric material such as one mil thick polyethylene film, and a moisture-pervious topsheet 6, which is typically comprised of either an elongatable non-woven fibrous material or an elongatable apertured polymeric film.

Particularly preferred materials which can be used for elastomeric elements or patches 4a include foams having an elongation to break of at least about 400% and an extension force of about 200 grams per inch of sample width at 50% extension of its unstrained length. Exemplary foams which have been found usable are: General Foam polyurethane foam No. 40310 having a no-load caliper or thickness of approximately 80 mils and a density of approximately 2.06 pounds per cubic foot (approximately 0.033 grams per cubic centimeter), as available from General Foam of Paramus, N.J.; Bridgestone SG polyurethane foam having a no-load caliper or thickness of approximately 80 mils and a density of about 2.06 pounds per cubic foot (0.033 grams per cubic centimeter), as available from Bridgestone of Yokohama, Japan; cross-linked natural rubber foam having a no-load caliper or thickness of approximately 50 mils and a density of about 13.3 pounds per cubic foot (0.214 grams per cubic centimeter), as available from Fulflex Inc. of Middleton, R.I.; and cross-linked natural rubber foam having a no-load caliper or thickness of approximately 50 mils and a density of about 13.3 pounds per cubic foot (0.24 grams per cubic centimeter), as available from Ludlow Composites Corporation of Fremont, Ohio.

Particularly preferred materials for backsheet 5 include blends comprised of about 45-90% linear low density polyethylene and about 10-55% polypropylene. If used in unembossed form, the backsheet 5 typically exhibits a no-load caliper or thickness of approximately 1 mil. If desired, the backsheet may be embossed to a caliper of approximately 5.5 mils to enhance the web's handling and appearance characteristics. Exemplary backsheet materials which have been found to work are: RR8220 blend REDEM, as available from Tredegar Industries, Inc. of Terre Haute, Ind.; and RR5475 blend ULAB, as available from Tredegar Industries, Inc. of Terre Haute, Ind.

One particularly preferred material for moisture pervious topsheet 6 comprises a hydrophobic, nonwoven carded web having a basis weight in the range of about 18-20 grams per square yard and comprised of approximately 2.2 denier polypropylene fibers, as available from Veratec, Inc., a Division of International Paper Company, of Walpole, Mass. under the designation P8.

A particularly desirable aesthetic appearance results in the "zero-strain"stretch laminate portions of the diaper web when the backsheet 5, the topsheet 6 or both are comprised of resilient three-dimensional polymeric webs of the type generally disclosed in commonly assigned U.S. Pat. No. 4,342,314 issued to Radel and Thompson on Aug. 31, 1982 and hereby incorporated herein by reference.

The continuous webs of backsheet material 5 and topsheet material 6 are preferably maintained under very slight (essentially "zero-strain") tension in the machine direction to prevent wrinkling and to facilitate registration with the diaper assembly and converting operations until the completed diaper web is severed into discrete diapers 2 at knife 22.

The diaper web forming operation is illustrated only schematically in FIG. 1. The absorbent pad segments 3 are fed into the nip between a pair of combining or laminating rolls 15 at regularly spaced, predetermined intervals. In a particularly preferred embodiment, the absorbent pad segments 3 are preferably comprised of airfelt confined within a cellulosic tissue envelope to provide pad integrity in use.

As has been pointed out earlier herein, "zero-strain"-stretch laminate webs of the present invention may be produced utilizing either an intermittent bonding configuration or a substantially continuous bonding configuration. The intermittent bonding configuration is normally desirable in those situations where the substantially inelastic webs in the laminate are relatively elongatable or drawable without rupture and where a high degree of z-direction bulking is desired in the finished laminate.

Conversely, a continuous bonding configuration has generally been found desirable where the degree of z-direction bulking is not of prime importance and one or more of the relatively inelastic webs in the laminate is difficult to elongate or draw without causing rupture. In the latter situation, a substantially continuous bonding configuration maintains all of the layers of the laminate in relatively close adherence to one another after the incremental stretching operation. Accordingly, even if one or more of the relatively inelastic webs is damaged to the point of rupture during the incremental stretching operation, the relatively close adherence of the damaged portions of the relatively inelastic web or webs to the elastomeric ply makes it difficult for the end user to perceive that any damage has occurred. Provided rupture of the relatively inelastic web or webs does not defeat the web's intended functionality, e.g., fluid-imperviousness, the damage which does occur to the relatively inelastic web or webs during the incremental stretching operation is not perceived as a negative in the end product.

Thus, an unexpected benefit which results from the use of a continuous bonding configuration in particularly preferred "zero strain" stretch laminate webs of the present invention is that it permits the manufacturer of the elasticized article to select from a much wider range of relatively inelastic webs which may be successfully employed in laminates of the present invention. In essence, it permits the use of relatively inelastic webs which would not normally be considered drawable to any appreciable extent in "zero-strain"stretch laminate webs of the present invention. Accordingly, unless expressly stated otherwise, the term "drawable" as used in the present specification and claims, is not intended to exclude relatively inelastic webs which undergo a degree of thinning or damage during the incremental stretching operation.

As can be seen in the embodiment of FIG. 1, the continuous web of moisture-impervious elongatable backsheet material is directed in close proximity to a glue applicator 10. If an intermittently bonded laminate web is desired in order to maximize the degree of z-direction bulking in the finished product, the glue applicator 10 may be used to apply discrete, spaced apart spots of adhesive in these predetermined areas of backsheet 5 where the substantially untensioned elastomeric patches 4a will be placed.

Alternatively, if a substantially continuously bonded laminate web is desired, the glue applicator 10 may be used to apply a substantially uniform and continuous application of adhesive 10a to the backsheet 5 in those predetermined areas where the substantially untensioned elastomeric patches 4a will be placed. In a particularly preferred embodiment of the latter type, the adhesive selected is stretchable and the glue applicator comprises a melt blown applicating system.

One such melt blown adhesive applicating system which Applicant has found particularly well suited for producing a substantially continuously bonded "zero-strain" stretch laminate web of the present invention is a melt blown spray applicator Model No. GM-50-2-1-GH, as available from J&M Laboratories of Gainesville, Ga. The latter system employs a nozzle having 20 orifices per lineal inch, as measured in the cross-machine direction, each orifice measuring approximately 0.020 inches in diameter. A Findley H-2176 Hot Melt Adhesive, as available from Findley Adhesives of Findley, Ohio is preferably heated to a temperature of approximately 340° F. and applied to the backsheet 5 at a rate of approximately 7.5–10 milligrams per square inch. Heated compressed air at a temperature of approximately 425° F. and a pressure of approximately 50 psig is issued through the secondary orifices in the adhesive nozzle to assist in uniformly distributing the adhesive fibrils during the laydown operation.

The intimate contact of the hot glue substantially shown as 10a in FIG. 1 with the backsheet web 5 for the time which passes prior to incremental stretching of the resultant "zero-strain" stretch laminate portion of the diaper web provides softening of the backsheet. For some webs, such as conventional polyethylene backsheet material, this softening has been found beneficial in minimizing damage to the backsheet during the incremental web stretching process. This may be particularly important in situations where the web in question imparts some function, e.g., fluid-imperviousness, to the finished article being produced.

Alternatively, the components comprising the "zero-strain" portions of the diaper web may be intermittently or continuously bonded to one another using unheated adhesive, heat bonding, pressure bonding, ultrasonic bonding, etc. In such instances, thermal energy may, if desired, be applied to the backsheet web 5 by other means well known to those skilled in the art, e.g., radiant heaters (not shown), hot air blasts (not shown), etc., to achieve a similar result.

Two rolls of elastomeric material 4 are fed under very slight (essentially "zero-strain") tension at a speed which provides the desired length of elastomeric patch 4a per diaper onto an anvil roll equipped with vacuum hold down ports (not shown) at its periphery. Knife 12 makes one cut per diaper and the substantially untensioned elastomeric patches 4a travel with anvil roll 11 secured to its periphery by vacuum until they reach transfer point 13. At point 13 the elastomeric patches 4a are transferred to predetermined portions of the backsheet web 5 coinciding with adhesive 10a, preferably by high pressure air blasts. The transfer is sequential and the surface speed of the vacuum equipped anvil roll and backsheet web 5 are essentially equal.

The backsheet web 5 with elastomeric patches 4a attached thereto at predetermined points along its length is then directed to the pair of laminating or combining rolls 15.

A continuous web of a moisture-pervious topsheet material 6, such as an elongatable fibrous nonwoven web, is directed in close proximity to a second glue applicator 14 where a pattern of adhesive 14a sized to substantially match the dimensions and locations of the elastomeric patches 4a on backsheet web 5 is preferably applied. As with the backsheet material 5, the pattern of adhesive applied to the topsheet material 6 may be either intermittent or substantially continuous, depending upon the properties of the topsheet material 6 and the characteristics desired in the resultant "zero-strain" stretch laminate web. If desired, adhesive applicator 14 may be identical to adhesive applicator 10.

The backsheet web 5 and topsheet web 6 and the absorbent pads 3 are brought into contact with one another at combining rolls 15. Just prior to the webs and pads coming into contact with one another, additional adhesive is preferably applied to one or both webs by means which are, for clarity, not shown in FIG. 1. The latter adhesive secures predetermined portions of the backsheet, the topsheet and the absorbent pad to one another to form the diaper web 1.

The fully assembled diaper web thereafter preferably proceeds through a pair of bond setting rolls 16, which may require chilling to minimize glue bleed through.

The fully assembled diaper web 1 is then directed through an incremental web stretching employing opposed pressure applicators having three dimensional surfaces which at least to a degree are complementary to one another system of the present invention, which is shown only schematically as 20 in FIG. 1. Details of a particularly preferred incremental web stretching system of the present invention which can be employed as system 20 are set forth in FIG. 2.

Referring to FIG. 2, timing of the diaper web 1 containing substantially untensioned elastomeric patches 4a is such that the substantially untensioned elastomeric patches 4a contained within the diaper web substantially coincide with the corrugated or grooved segments 24 contained on uppermost corrugated rolls 25 as the diaper web 1 passes between the segments 24 of uppermost corrugated rolls 25 and the continuously corrugated or grooved lowermost corrugated rolls 21. If desired, the grooved segments 24 may be of greater overall length than the elastomeric patches 4a, as measured in the machine direction, so as to impart a degree of extensibility to those portions of the topsheet and backsheet which are adjacent the elastomeric patches 4a in the finished diaper.

While the exact configuration, spacing and depth of the complementary grooves on the uppermost and lowermost corrugated rolls will vary, depending upon such factors as the amount of elasticity desired in the "zero-strain" stretch laminate portion of the fully processed web, two pairs of sequenced corrugated rolls, each having a peak-to-peak groove pitch of approximately 0.150 inches, an included angle of approximately 12° as measured at the peak, and a peak-to-valley groove depth of approximately 0.300 inches have been employed in a particularly preferred embodiment of the present invention. The exterior peak of each corrugation on the aforementioned corrugated roll pairs exhibits a radius of approximately 0.010 inches, while the internal groove formed between adjacent corrugations typically exhibits a radius of approximately 0.040 inches. The sequenced corrugated roll pairs are typically adjusted so that the opposing peaks on each succeeding pair of meshing corrugated rolls increase their degree of overlap with one another approximately 0.035–0.050 inches from the first pair of meshing corrugated rolls to the second pair, the second set of meshing corrugated rolls typically overlapping one another to a total depth between about 0.150 inches and about 0.175 inches. Two pairs of meshing corrugated rolls of the aforementioned type mounted in sequence with one another have produced good elastic characteristics in a laminate web of the present invention comprised of 80 mil thick elastomeric polyurethane foam patches 4a substantially continuously bonded on their opposed surfaces to a one mil thick moisture impervious polymeric backsheet 5 and a hydrophobic nonwoven topsheet 6 having a basis weight in the range of about 18 to 20 grams per square yard and comprised of approximately 2.2 denier polypropylene fibers.

The degree of overlap of the opposing peaks on the successive pairs of meshing corrugated rolls may of course be adjusted, as desired, to produce more or less extensibility in the resultant "zero-strain"stretch laminate portion of the web. For the aforementioned roll geometry and laminate web construction, peak-to-peak overlap depths ranging from as little as about 0.050 inches to as much as about 0.225 inches are feasible. In general, as the number of sequenced meshing corrugated roll pairs increases for any given total amount of incremental stretching, the potential for web damage decreases. This is believed due to the fact that the incremental stretching operation is carried out more gradually in a series of relatively small steps when a series of sequenced meshing corrugated roll pairs is employed. More gradual stretching of the web is believed to minimize damage to the web.

Figure 2A:
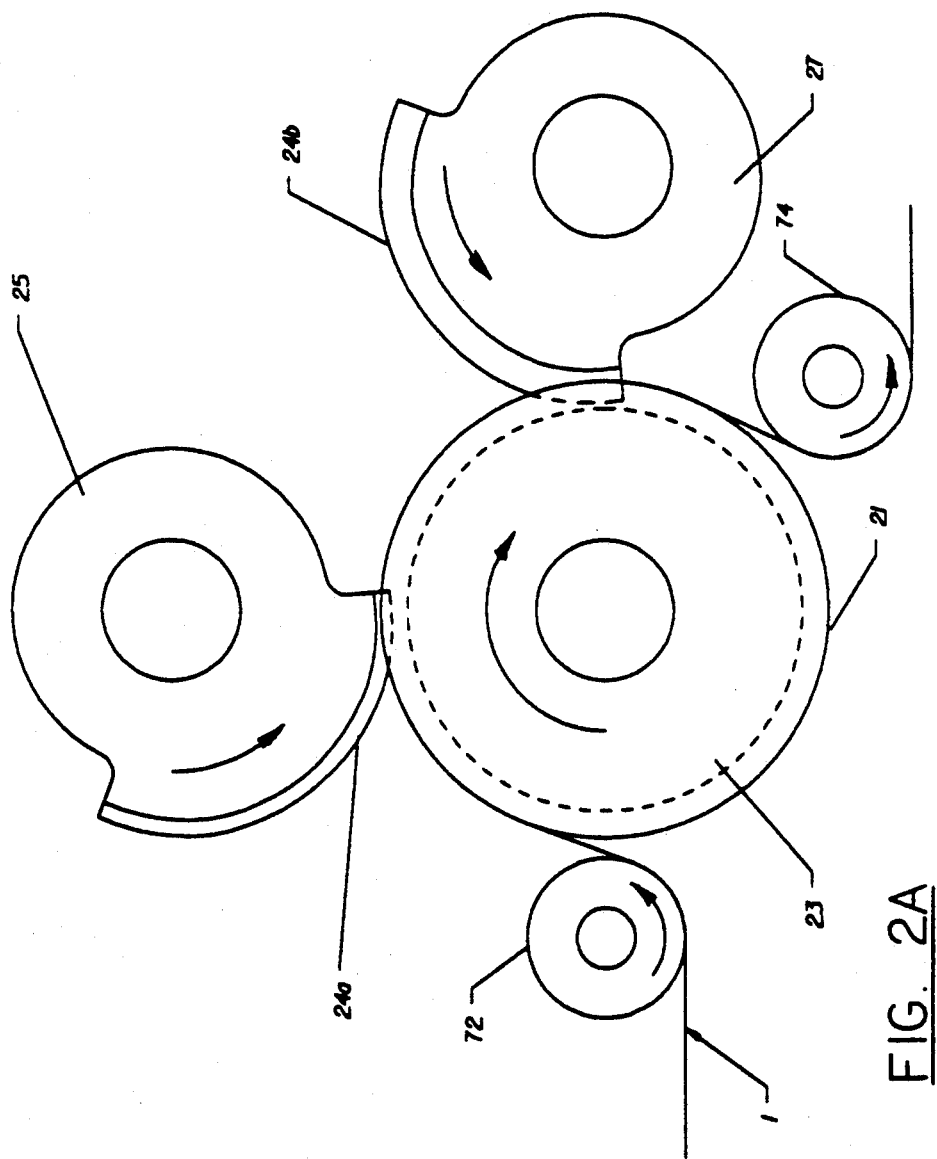
FIG. 2A is a simplified view taken along view line 2A—2A in FIG. 2 and showing the manner in which idler rolls are used to cause the diaper web to wrap lowermost corrugated rolls.

As can be seen from FIG. 2A, the diaper web 1 is caused by idler rolls 72,74 to wrap the lowermost corrugated rolls 21 sufficiently to cover the active vacuum ports 22 located immediately adjacent each continuous set of grooves 23 on lowermost rolls 21. The vacuum ports 22, which are positioned so as to substantially coincide with the grooved segments 24 on uppermost corrugated rolls 25, are internally connected through rolls 21 to a pair of vacuum manifolds 26 which exert suction against the diaper web 1 as the diaper web is acted upon by the grooved segments 24 of uppermost corrugated rolls 25.

To minimize build up of either the adhesive used to secure the untensioned elastomeric patches 4a to the fluid-pervious topsheet web 6 and the fluid-impervious backsheet web 5 or the adhesive used to secure the coinciding portions of the topsheet web and the backsheet web to one another, the grooved segments 24 on uppermost rolls 25 and the continuous grooves 23 on lowermost rolls 21 are preferably either comprised of a low friction material, such as TEFLON ®(Polytetrafluoroethylene), or coated with a self-lubricating low friction material such as an aqueous dispersion of a fortified fluoropolymer, for example PERMALON ® No. 503 spray coating, as available from Micro Surface Corporation of Morris, Ill.

The vacuum ports 22 on lowermost rolls 21 are preferably covered by a porous material, such as 0.090" mesh honeycomb 44, to provide support to the portions of the diaper web 1 acted upon by the vacuum and to provide a good gripping surface against the web so as to substantially prevent lateral slippage or movement of the web across the honeycomb surface whenever the web is acted upon by vacuum.

Under optimum circumstances, the maximum degree of incremental stretching which can be imparted to the "zero-strain" portions of the diaper web 1 containing elastomeric patches 4a is determined by the depth of engagement between the grooves on segments 24 of uppermost corrugated rolls 25 and the continuous grooves 23 on lowermost corrugated rolls 21. However, Applicant has discovered that unless the stretch laminate web is substantially prevented from slipping or contracting in a direction substantially parallel to the direction of web stretching as it passes between the meshing corrugated rolls, the optimum degree of incremental stretching is not realized. Therefore, in its most preferred form, the incremental web stretching operation of the present invention is carried out while the outermost portions of all of three layers comprising the "zero strain" stretch laminate composite are subjected to restraint, as generally shown in the cross-section of FIG. 2B, to substantially prevent the "zero-strain"-stretch laminate portions of the diaper web from slipping or contracting in a direction parallel to the desired direction of stretching as it passes between the sets of sequentially positioned meshing corrugated rolls.

However, the present invention may also, if desired, be practiced to advantage by restraining only the elongatable or drawable layer or layers of the composite, i.e., it is not an absolute requirement that the outermost portions of the elastomeric elements 4a also be restrained during the incremental stretching operation. In the latter instance, the elongatable or drawable layer or layers are still permanently elongated during the incremental stretching process, but the z-direction bulking in the resultant "zero-strain"stretch laminate web may be somewhat less pronounced when the stretching tension is removed. This is due to the fact that the elastomeric layer undergoes a lesser degree of initial stretching during such a process. Accordingly, it can only undergo this same amount of retraction when it returns to its undistorted configuration.

A "zero-strain"stretch laminate embodiment of the aforementioned type may also exhibit some degree of disproportionate straining in the elongatable web or webs in the areas immediately adjacent the opposed edges of the elastomeric elements 4a. In the case of an opaque polymeric backsheet web which is normally employed as a fluid-impervious barrier on a diaper, these disproportionately strained portions can become sufficiently thinned that they may even appear transparent despite the fact no rupture has taken place. In such instances the functionality, e.g., the fluid-imperviousness, of the "zero-strain"stretch laminate portions of the diaper web is not impaired. Embodiments of the latter type are normally employed in situations where the aesthetic appearance of the "zero-strain"stretch laminate portion of the resultant article is either hidden from view by the design or configuration of the article or, if visible, is of no concern to the user of the article.

In still another embodiment of the present invention even rupture of one or more of the elongatable nonelastic webs may not render the resultant "zero-strain"-stretch laminate web unacceptable for its intended purpose, e.g., rupture of the backsheet web 5 does not necessarily destroy the laminate web's functionality for its intended purpose as long as one of the other plies in the laminate web provides the desired function in the finished article. For example, some degree of rupturing in the elongatable backsheet web 5 will not destroy the fluid-imperviousness of the resultant disposable diaper web if the elastomeric patches 4a are comprised of a fluid-impervious material. This is particularly true with respect to those "zero-strain"stretch laminate web embodiments employing substantially continuous bonding between the plies in question, since relatively close adherence of the plies to one another after incremental stretching renders such ply damage difficult to detect by the end user of the article.

Because the diaper web 1 shown in FIGS. 1-2B is substantially impervious to the passage of air by virtue of the presence of the uppermost moisture-impervious backsheet web 5, vacuum ports 22 covered by porous honeycomb material 44 can, if desired, be employed immediately adjacent each set of machine direction oriented grooves 23 in lowermost corrugated rolls 21. If the elastomeric patches 4a are sufficiently pervious to the passage of air, the suction forces generated by the vacuum will pass through the fluid-pervious topsheet web 6 and the elastomeric patches so as to tightly grip the overlying portions of the backsheet 5. In this instance, all three layers comprising the "zero-strain"-stretch laminate portions of the diaper web will be restrained during the incremental stretching operation.

If the elastomeric patches 4a were not substantially pervious to the passage of air, it would be necessary to either (a) position the vacuum ports 22 and the overlying honeycomb material 44 just outside the opposed edges of the elastomeric patches 4a so that suction forces could be exerted on the fluid-impervious drawable backsheet web 5 through the fluid-pervious drawable topsheet web 6; or (b) restrain all three layers comprising the "zero-strain"stretch laminate portions of the diaper web by means of suitable clamping apparatus capable of acting upon the opposed surfaces of the diaper web Such apparatus are disclosed in the aforementioned concurrently filed, commonly assigned U.S. patent application of Gerald M. Weber, William R. Vinnage, Jr., Douglas H. Benson and David A. Sabatelli entitled IMPROVED METHOD AND APPARATUS FOR INCREMENTALLY STRETCHING ZERO STRAIN STRETCH LAMINATE WEB TO IMPART ELASTICITY THERETO, Ser. No. 662,536 filed Feb. 28, 1991, the disclosure of which is hereby incorporated herein by reference.

The suction forces applied to the diaper web 1 shown in Drawing FIGS. 1-2C by vacuum ports 22 acting through porous honeycomb material 44 substantially prevent those portions of the diaper web containing substantially untensioned elastomeric patches 4a from slipping or contracting in a laterally inward direction as they pass between the meshing portions of the continuous grooves 23 on lowermost corrugated rolls 21 and the grooved segments 24a and 24b of the first and second sets of uppermost corrugated rolls 25 and 27, respectively.

This not only maximizes the effectiveness of the incremental web stretching operation by forcing the elongatable topsheet and backsheet webs secured to the elastomeric patches 4a to undergo the fullest possible degree of elongation during the stretching operation, but also substantially prevents disproportionately high straining of the topsheet and/or backsheet webs to which they are secured in the areas immediately adjacent the opposed peripheral edge portions of the elastomeric patches.

Sequentially stretching the "zero-strain"stretch laminate portions of the diaper web 1 in accordance with the present invention using multiple pairs of meshing corrugated rolls, each subsequent pair of corrugated rolls exhibiting an increased degree of meshing, reduces the rate at which the elongation process is carried out and hence the rate at which strain is experienced by the composite web as it passes therebetween. In addition, the temporary release of tension from the web as it passes between the successive roll pairs allows some degree of stress redistribution to occur in the web prior to the web's being incrementally stretched to a greater degree by each succeeding roll pair.

Therefore, the more meshing roll pairs which are used to achieve the desired degree of incremental stretching, the more gradual will be the stretching of the web as it passes between any given roll pair and the more opportunities there will be provided for stress redistribution to occur within the web. This not only minimizes the rate at which strain is experienced by the composite web, but maximizes the opportunities for stress redistribution between each incremental stretching operation. Consequently a sequential roll system of the present invention is less prone to cause damage to the webs being processed than if the entire stretching operation is carried out on a single roll pair exhibiting an equivalent degree of meshing.

Figure 2D:
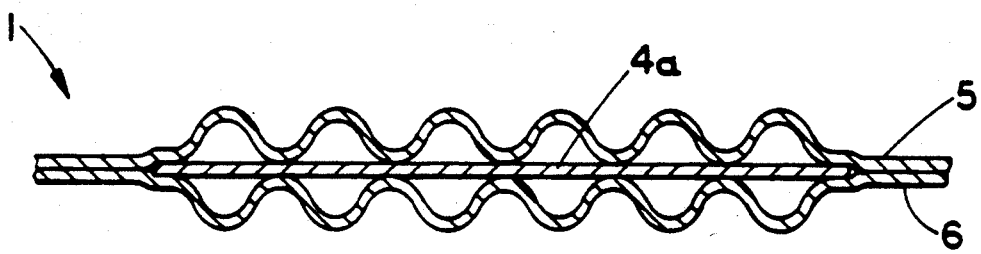
FIG. 2D is a highly enlarged simplified cross-sectional view of an intermittently bonded "zero-strain"-stretch laminate web of the present invention after the web has passed through a corrugated roll nip of the type shown in FIGS. 2B and 2C.
Figure 2E:
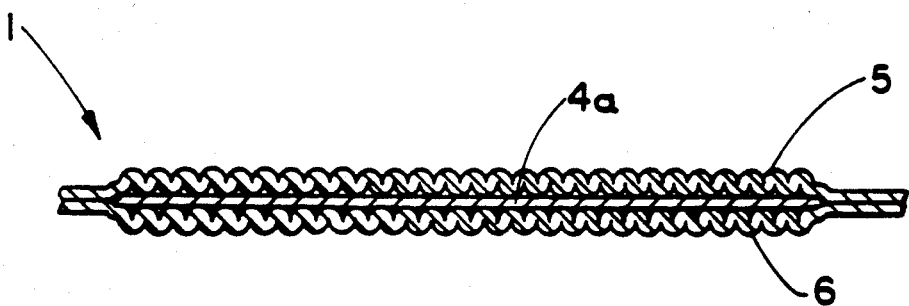
FIG. 2E is a highly enlarged simplified cross-sectional view of a substantially continuously bonded "zero-strain" stretch laminate web of the present invention after the web has passed through a corrugated roll nip of the type shown in FIGS. 2B and 2C.

The cross-section of FIG. 2D reveals the condition of an untensioned intermittently bonded "zero-strain"-stretch laminate web of the present invention, as viewed at a point corresponding to its greatest degree of incremental stretching, while the cross-section of FIG. 2E reveals the condition of an otherwise identical untensioned substantially continuously bonded "zero-strain"-stretch laminate web of the present invention, as viewed at a point corresponding to its greatest degree of incremental stretching. Although both webs are elastically extensible in the direction of initial stretching, at least up to the point of initial stretching, the intermittently bonded "zero-strain"stretch laminate web shown in FIG. 2D exhibits a much greater degree of z-direction bulking.

Following the sequential incremental stretching operation shown schematically as 20 in FIG. 1, the fully assembled diaper web 1 is preferably passed through a side notching apparatus shown schematically as 60, wherein notches intended to coincide with the wearer's legs are cut from the lateral edge portions of the fully assembled diaper web.

Finally, the diaper web 1 is cut at predetermined locations along its length by means of knife 22 to produce hourglass-shaped single use diapers having at least one pair of substantially undamaged side panels which are elastically extensible, in a direction substantially parallel to the diaper's waistband, at least up to the point of initial stretching.

From the description contained herein, it is clear that the improved method and apparatus of the present invention may be employed to advantage to produce a wide range of elasticized articles either comprised entirely of or including one or more discrete, isolated "zero-strain"stretch laminate web portions.

It is also recognized that while sequentially positioned pairs of meshing corrugated rolls having their corrugations aligned substantially parallel to one another are disclosed in the accompanying Drawing Figures, the present invention may be practiced with equal facility employing sequentially positioned pairs of corrugated rolls wherein the corrugations are not all oriented parallel to one another. Furthermore, the corrugations on such sequentially positioned pairs of corrugated rolls need not necessarily be aligned parallel to either the machine or the cross-machine direction. For example, if a curvilinear waistband or legband portion is desired in a single use diaper constructed using the "zero-strain"stretch laminate technology herein disclosed, the meshing teeth on the sequentially positioned pairs of corrugated rolls employed to sequentially stretch the "zero-strain"portions of the diaper web may be arrayed in the desired curvilinear configuration to produce elasticity along the desired curvilinear contour rather than in a straight line.

It is further recognized that while the preferred high speed processes herein disclosed employ sequentially positioned pairs of meshing cylindrical corrugated rolls, the sequential web stretching operation of the present invention may also be carried out utilizing a sequential intermittent stamping operation employing multiple sets of meshing platens, each set having a greater degree of meshing than the prior set, to sequentially stretch the "zero-strain" stretch laminate portions of a web or an article placed between the platens.

Figure 3:
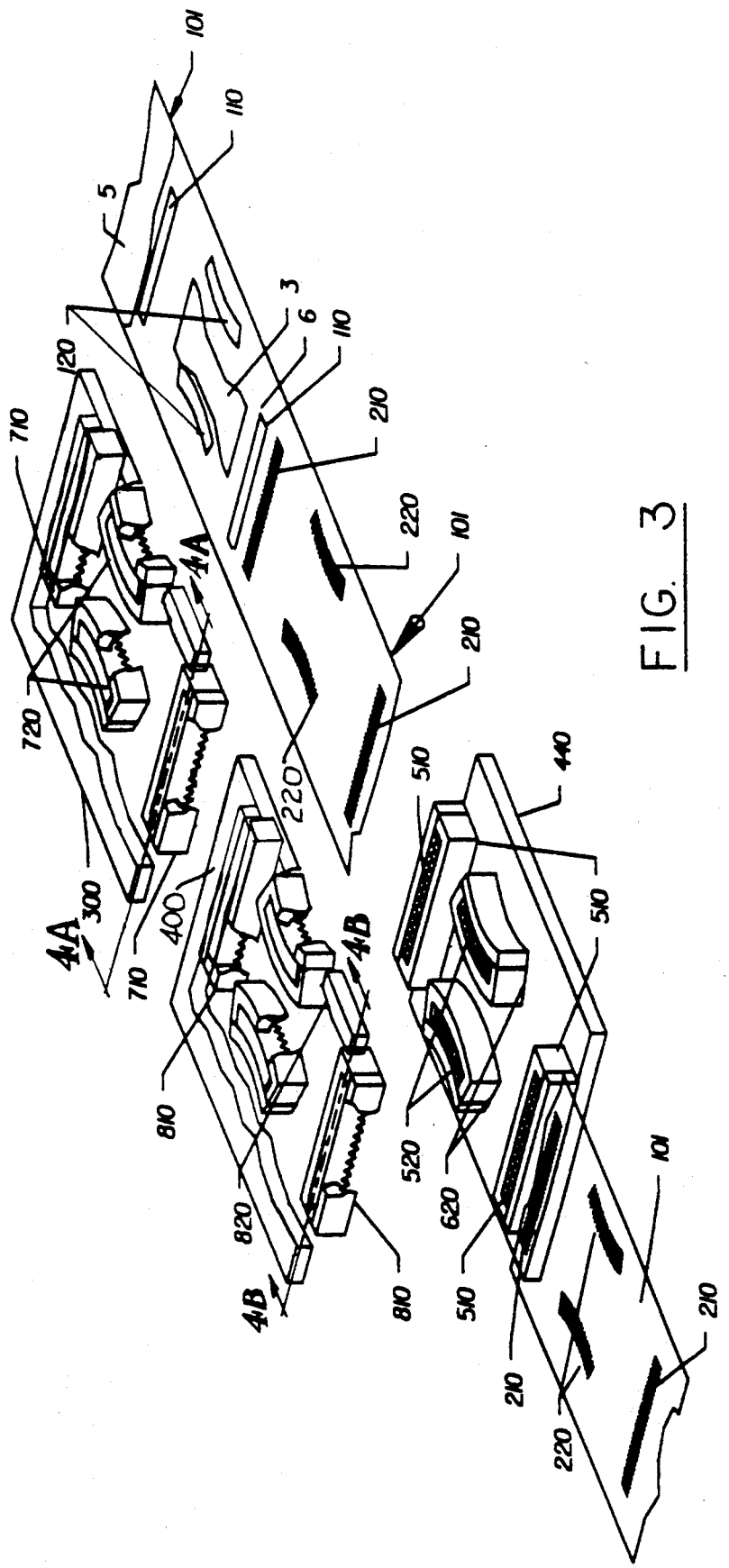
FIG. 3 is a simplified schematic illustration of an alternative sequential web stretching system of the present invention.

Such a sequential stamping operation is illustrated schematically in FIG. 3. The diaper web 101 therein disclosed comprises a fluid-pervious topsheet 6, a fluid-impervious backsheet 5, absorbent pads 3 and substantially untensioned elastomeric patches 110 and 120 which form "zero-strain"stretch laminate waistband portions 210 and curvilinear "zero-strain"stretch laminate legband portions 220, respectively, in the diaper web.

The diaper web 101 is sequentially passed through at least two pairs of meshing platens. The bottom platen 440, which includes curvilinear teeth 520 for incrementally stretching the legband portions of the diaper web and straight teeth 510 for incrementally stretching the waistband portions of the diaper web is first engaged, with diaper web 101 supported thereon, by an uppermost meshing platen 300 having toothed sections complementary to those on bottom platen 440. A typical cross-section of the teeth employed on uppermost platen 300 is shown in FIG. 4A. Tension on the partially stretched diaper web 101 is temporarily released, and the diaper web remains on the bottom platen 440 until a second uppermost platen 400, which employs complementary teeth having a greater amplitude than those on platen 300, as generally shown in the cross-section of FIG. 4B, repeats the stamping operation on the partially stretched "zero strain" stretch laminate portions of the diaper web. As a result, the "zero-strain"stretch laminate portions 210,220 of the diaper web 101 are sequentially stretched without damage.

To ensure that the maximum degree of incremental web stretching is achieved, the toothed segments 510,520 on lowermost platen 440 are preferably surrounded by resiliently deformable windows 610,620 which contact and clamp the "zero-strain"stretch laminate portions 210,220 of the diaper web 101 about their periphery against corresponding sets of non-deformable windows 710,720 and 810,820 surrounding the complementary teeth on uppermost platens 300 and 400, respectively. This clamping action prevents slippage or contraction of the "zero-strain"stretch laminate portions of the web in a direction substantially parallel to the direction of stretching during the incremental stretching operations performed on the successive sets of meshing platens. The resiliently deformable windows 610,620 must, of course, deform sufficiently to permit the desired degree of meshing between the teeth on uppermost platens 300 and 400 and the opposing teeth 510,520 on lowermost platen 440 during the sequential stretching operation.

Alternatively, those "zero-strain"stretch laminate portions 210,220 of the diaper web 101 to be sequentially stretched may be restrained by suitable vacuum means (not shown) surrounding the toothed segments 510,520 on lowermost platen 440 before either of the uppermost meshing platens 300 or 400 is able to exert enough force on the "zero-strain"stretch laminate portions of the diaper web to cause slippage or contraction thereof in a direction parallel to the direction of stretching.

While the present invention has been described primarily in the context of providing elasticized ears or elasticized waistbands and/or legbands in a single use diaper, it is recognized that the present invention may also be practiced to advantage in many other applications and environments. It will be obvious to those skilled in the art that various changes and modifications can be made without departing from the spirit and scope of the present invention, and it is intended to cover in the appended claims all such modifications that are within the scope of this invention.

What is claimed is:

1. An improved method for sequentially stretching a zero strain stretch laminate web to impart elasticity thereto in the direction of stretching, at least up to the point of initial stretching, without rupturing said zero strain stretch laminate web, said method comprising the steps of:
   (a) feeding a zero strain stretch laminate web comprising a substantially untensioned first elastomeric ply intermittently secured to a substantially untensioned second ply comprising a continuous web which is elongatable, but which exhibits less elastic recovery than said first ply, between a first pair of opposed pressure applicators having three-dimensional surfaces which, at least to a degree, are complementary to one another;
   (b) subjecting the portions of said zero strain stretch laminate web located between said first pair of opposed pressure applicators to incremental stretching by causing said three-dimensional surfaces of said first pair of opposed pressure applicators to mesh with one another, at least to a degree, whereby said second elongatable ply is permanently elongated, at least to a degree, by said initial incremental stretching;
   (c) removing at least one of said first pair of pressure applicators from contact with the surface of said initially stretched portion of said zero strain stretch laminate web, thereby relieving the stretching tension on said initially stretched portion of said laminate web; and
   (d) subjecting said initially stretched portions of said zero strain stretch laminate web to further incremental stretching by contacting the exposed surface of said partially stretched zero strain stretch laminate web with a second pair of opposed pressure applicators having three-dimensional surfaces which are also, at least to a degree, complementary to one another, but which mesh to a greater degree than said first pair of opposed pressure applicators, whereby said second elongatable ply is further permanently elongated with minimal damage by said sequential stretching operations so that said laminate web is elastically extensible in the direction of incremental stretching, at least up to the point of stretching by said second pair of opposed pressure applicators, and the width of said laminate web measured in said direction of stretching is substantially the same as before said initial stretching was applied once the incremental stretching forces are removed from said zero strain stretch laminate web.

2. An improved method for sequentially stretching a zero strain stretch laminate web to impart elasticity thereto in the direction of stretching, at least up to the point of initial stretching, without rupturing said zero strain stretch laminate web, said method comprising the steps of:

(a) feeding a zero strain stretch laminate web comprising
a substantially untensioned first elastomeric ply substantially continuously secured to a substantially untensioned second ply comprising a continuously web which is elongatable, but which exhibits less elastic recovery than said first ply, between a first pair of opposed pressure applicators having three-dimension surfaces which, at least to a degree, are complementary to one another;

(b) subjecting the portions of said zero strain stretch laminate web located between said first pair of opposed pressure applicators to incremental stretching by causing said three-dimension surfaces of said first pair of opposed pressure applicators to mesh with one another, at least to a degree, whereby said second elongatable ply is permanently elongated, at least to a degree, by said initial incremental stretching;

(c) removing at least one of said first pair of pressure applicators from contact with the surface of said initially stretched portion of said zero strain stretch laminate web, thereby relieving the stretching tension on said initially stretched portion of said laminate web; and (d) subjecting said initially stretched portions of said zero strain stretch laminate web to further incremental stretching by contacting the exposed surface of said partially stretched zero strain stretch laminate web with a second pair of opposed pressure applicators having three-dimensional surfaces which are also, at least to a degree, complementary to one another, but which mesh to a greater degree than said first pair of opposed pressure applicators, whereby said second elongatable ply is further permanently elongated with minimal damage by said sequential stretching operations so that said laminate web is elastically extensible in the direction of incremental stretching, at least up to the point of stretching by said second pair of opposed pressure applicators, and the width of said laminate web measured in said direction of stretching is substantially the same as before said initial stretching was applied once the incremental stretching forces are removed from said zero strain stretch laminate web.

3. The method of claim 1 or claim 2, wherein one of said first pair of pressure applicators is common to said second pair of pressure applicators.

4. The method of claim 1 or claim 2, wherein said sequential incremental stretching of said zero strain stretch laminate web is carried out in a direction which is substantially parallel to the direction of web travel.

5. The method of claim 1 or claim 2, wherein said sequential incremental stretching of said zero strain stretch laminate web is carried out in a direction which is substantially perpendicular to the direction of web travel.

6. The method of claim 1 or claim 2, wherein said sequential incremental stretching of said zero strain stretch laminate web is carried out in a non-linear configuration.

7. The method of claim 6, wherein said sequential incremental stretching of said zero strain stretch laminate web is carried out in a multiplicity of directions.

8. The method of claim 1 or claim 2, wherein said zero strain stretch laminate web further comprises a third substantially untensioned ply which is elongatable, but which exhibits less elastic recovery than said first elastomeric ply, secured to the surface of said first substantially untensioned elastomeric ply which is opposite said second substantially untensioned ply.

9. The method of claim 8, wherein said second substantially untensioned ply is moisture-impervious.

10. The method of claim 9, wherein said second substantially untensioned ply is comprised of polymeric film.

11. The method of claim 10, wherein said second substantially untensioned ply comprises a resilient three-dimensional polymeric film.

12. The method of claim 8, wherein said third substantially untensioned ply is moisture-pervious.

13. The method of claim 12, wherein said third substantially untensioned, moisture-pervious ply is comprised of a non-woven fibrous material.

14. The method of claim 12, wherein said third substantially untensioned ply comprises a resilient apertured three-dimensional polymeric film.

15. An improved method for sequentially stretching a continuously moving zero strain stretch laminate web to impart elasticity thereto in the direction of stretching, at least up to the point of initial stretching, without rupturing said zero strain stretch laminate web, said method comprising the steps of:

(a) continuously feeding a zero strain stretch laminate web comprising a substantially untensioned first elastomeric ply intermittently secured to a substantially untensioned second ply comprising a continuous web which is elongatable, but which exhibits less elastic recovery than said first ply, between a first pair of opposed pressure applicators comprising corrugated rolls having an axis of rotation perpendicular to the direction of web travel, said corrugated rolls having three-dimensional surfaces comprising corrugations which, at least to a degree, are complementary to one another;

(b) subjecting the portions of said continuously moving zero strain stretch laminate web located between said first pair of opposed pressure applicators to incremental stretching by causing said three-dimension surfaces of said first pair of opposed pressure applicators to mesh with one another, at least to a degree, as said continuously moving web passes therebetween, whereby said second elongatable ply is permanently elongated, at least to a degree, by said initial incremental stretching;

(c) removing at least one of said first pair of pressure applicators from contact with the surface of said initially stretched portion of said continuously moving zero strain stretch laminate web, thereby relieving the stretching tension on said initially stretched portion of said laminate web; and (d) subjecting said initially stretched portions of said continuously moving zero strain stretch laminate web to further incremental stretching by contacting the exposed surface of said partially stretched zero strain stretch laminate web with a second pair of opposed pressure applicators comprising corrugated rolls having an axis of rotation perpendicular to the direction of web travel and three-dimensional surfaces comprising corrugations which are also, at least to a degree, complementary to one another, but which mesh to a greater degree than said first pair of opposed pressure applicators, whereby said second elongatable ply is further permanently elongated with minimal damage by said sequential stretching operations so that said laminate web is elastically extensible in the direction of incremental stretching, at least up to the point of stretching by said second pair of pressure applicators, and the width of said laminate web measured in said direction of stretching is substantially the same as before said initial stretching was applied once the incremental stretching forces are removed from said zero strain stretch laminate web.

16. An improved method for sequentially stretching a continuously moving zero strain stretch laminate web to impart elasticity thereto in the direction of stretching, at least up to the point of initial stretching, without rupturing said zero strain stretch laminate web, said method comprising the steps of:

(a) continuously feeding a zero strain stretch laminate web comprising a substantially untensioned first elastomeric ply substantially continuously secured to a substantially untensioned second ply comprising a continuous web which is elongatable, but which exhibits less elastic recovery than said first ply, between a first pair of opposed pressure applicators comprising corrugated rolls having an axis of rotation perpendicular to the direction of web travel, said corrugated rolls having three-dimensioned surfaces comprising corrugations which, at least to a degree, are complementary to one another;

(b) subjecting the portions of said continuously moving zero strain stretch laminate web located between said first pair of opposed pressure applicators to incremental stretching by causing said three-dimensional surfaces of said first pair of opposed pressure applicators to mesh with one another, at least to a degree, as said continuously moving web passes therebetween, whereby said second elongatable ply is permanently elongated, at least to a degree, by said initial incremental stretching;

(c) removing at least one of said first pair of pressure applicators from contact with the surface of said initially stretched portion of said continuously moving zero strain stretch laminate web, thereby relieving the stretching tension on said initially stretched portion of said laminate web; and (d) subjecting said initially stretched portions of said continuously moving zero strain stretch laminate web to further incremental stretching by contacting the exposed surface of said partially stretched zero strain stretch laminate web with a second pair of opposed pressure applicators comprising corrugated rolls having an axis of rotation perpendicular to the direction of web travel and three-dimensional surfaces comprising corrugations which are also, at least to a degree, complementary to one another, but which mesh to a greater degree than said first pair of opposed pressure applicators, whereby said second elongatable ply is further permanently elongated with minimal damage by said sequential stretching operations so that said laminate web is elastically extensible in the direction of incremental stretching, at least up to the point of stretching by said second pair of opposed pressure applicators, and the width of said laminate web measured in said direction of stretching is substantially the same as before said initial stretching was applied once the incremental stretching forces are removed from said zero strain stretch laminate web.

17. The method of claim 15 or claim 16, wherein one of said first pair of pressure applicators is common to said second pair of pressure applicators.

18. The method of claim 17, wherein the opposed peripheral edge portions of said continuously moving zero strain stretch laminate web are restrained during each stage of the incremental stretching operation to substantially prevent slippage or contraction of said web in a direction parallel to the direction of incremental stretching.

19. The method of claim 18, wherein said sequential incremental stretching of said zero strain stretch laminate web is carried out in a direction which is substantially parallel to the direction of web travel.

20. The method of claim 18, wherein said sequential incremental stretching of said zero strain stretch laminate web is carried out in a direction which is substantially perpendicular to the direction of web travel.

21. The method of claim 18, wherein said sequential incremental stretching of said zero strain stretch laminate web is carried out in a non-linear configuration.

22. The method of claim 18, wherein said sequential incremental stretching of said zero strain stretch laminate web is carried out in a multiplicity of directions.

* * * * *

UNITED STATES PATENT AND TRADEMARK OFFICE
CERTIFICATE OF CORRECTION

PATENT NO. : 5,143,679
DATED : September 1, 1992
INVENTOR(S) : GERALD M. WEBER and JAMES W. RICHARDSON It is certified that error appears in the above-identified patent and that said Letters Patent is hereby corrected as shown below:

Column 7, line 21, delete "30,232" and insert therefor -- 230,232 --.

Column 10, line 14, delete "therebetween:" and insert therefor -- therebetween; --.

Column 10, line 24, delete " 2C:" and insert therefor -- 2C; --.

Column 11, line 28, delete "0.24" and insert therefor -- 0.214 --.

Column 13, line 2, after "applicator" insert -- 10 --.

Column 14, line 20, after "stretching" insert -- system of the present invention --.

Column 14, line 23, delete "system of the present invention".

Column 17, line 27, after "web" insert -- 1. --.

UNITED STATES PATENT AND TRADEMARK OFFICE
CERTIFICATE OF CORRECTION

PATENT NO. : 5,143,679
DATED : September 1, 1992
INVENTOR(S) : GERALD M. WEBER and JAMES W. RICHARDSON It is certified that error appears in the above-identified patent and that said Letters Patent is hereby corrected as shown below:

Column 21, lines 11-12, delete "continuously" and insert therefor -- continuous --.

Column 21, line 15, delete "three-dimension" and insert therefor -- three-dimensional --.

Column 21, line 21, delete "three-dimension" and insert therefor -- three-dimensional --.

Column 22, line 51, delete "three-dimension" and insert therefor -- three-dimensional --.

Column 23, lines 35-36, delete "three dimensioned" and insert therefor -- three-dimensional --.

Signed and Sealed this

Fifth Day of October, 1993

Attest:

BRUCE LEHMAN

Attesting Officer     Commissioner of Patents and Trademarks